United States Patent [19]

Garbe

[11] Patent Number: 4,640,293
[45] Date of Patent: Feb. 3, 1987

[54] SPIROMETER ACCESSORY

[76] Inventor: Dietmar R. Garbe, Maids Moreton House, Maids Moreton, Buckingham, England

[21] Appl. No.: 692,704

[22] Filed: Jan. 18, 1985

Related U.S. Application Data

[63] Continuation of Ser. No. 430,689, Sep. 30, 1982, abandoned, which is a continuation of Ser. No. 201,286, Oct. 27, 1980, abandoned.

[30] Foreign Application Priority Data

Oct. 27, 1979 [GB] United Kingdom ................. 7937320
Sep. 23, 1980 [GB] United Kingdom ................. 8030676

[51] Int. Cl.$^4$ ............................................... A61B 5/08
[52] U.S. Cl. .................................... 128/716; 128/720; 128/725; 128/205.24; 137/908; 137/854; 137/856
[58] Field of Search .............. 128/716, 720, 725, 726, 128/727, 728, 729, 207.12, 207.16, 207.11, 201.11, 203.11, 205.13, 205.24, 202.28; 272/99 R; 137/854, 454.2, DIG. 9, 512.15, 851, 856, 859

[56] References Cited

U.S. PATENT DOCUMENTS

| 162,598 | 4/1875 | Bailey | 137/854 |
| 3,228,418 | 1/1966 | Rosback et al. | 137/854 |
| 3,256,910 | 6/1966 | Cupp | 128/207.12 |
| 3,262,447 | 7/1966 | Burke | 128/207.16 |
| 3,949,737 | 4/1976 | Nielsen | 128/726 |
| 4,253,468 | 3/1981 | Lehmbeck | 128/726 |

Primary Examiner—Henry J. Recla
Attorney, Agent, or Firm—A. W. Breiner

[57] ABSTRACT

A mouthpiece for the inlet tube of a spirometer is formed to engage the inlet end of the tube and has a radially extending part or parts for preventing reverse fitting. An apertured valve seating has a valve diaphragm of flexible material for obstructing the return flow of air to the patient's mouth. The seating may have a projecting rim for engagement with the peripheral region of the diaphragm, and the diaphragm is preferably mounted so that it is planar on first engagement therewith. A ring may be arranged to be contacted by the diaphragm after initial bulging by back-pressure. Further deformation of the diaphragm is thereby controlled so that its peripheral region remains in engagement with the rim.

8 Claims, 9 Drawing Figures

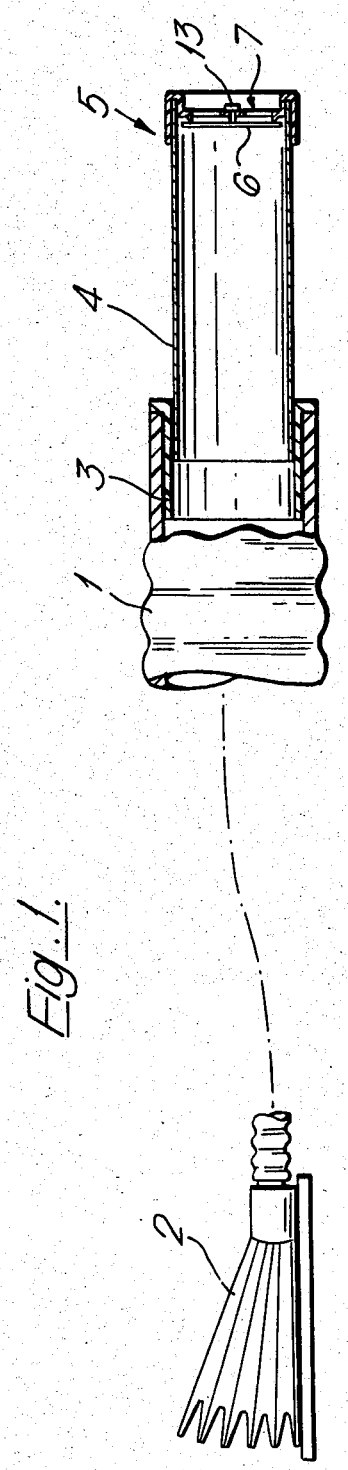
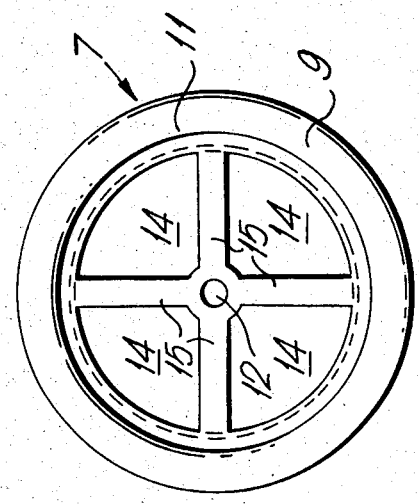
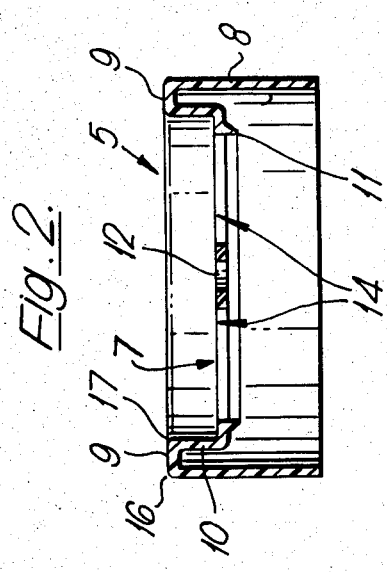

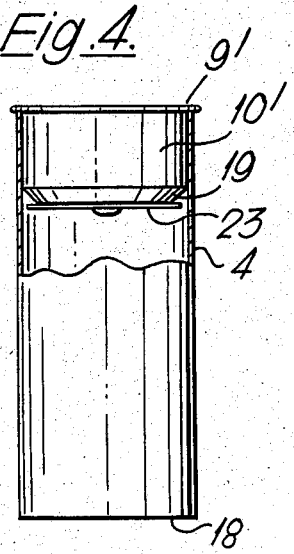
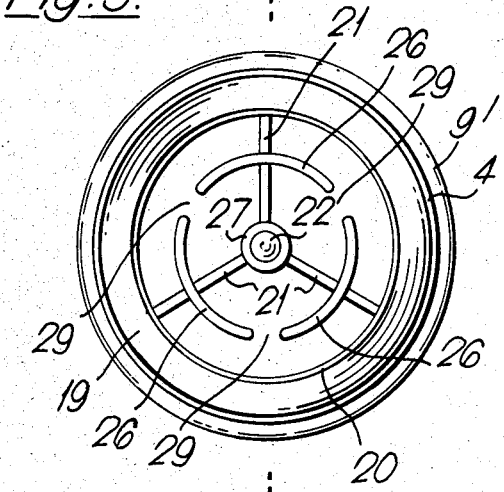
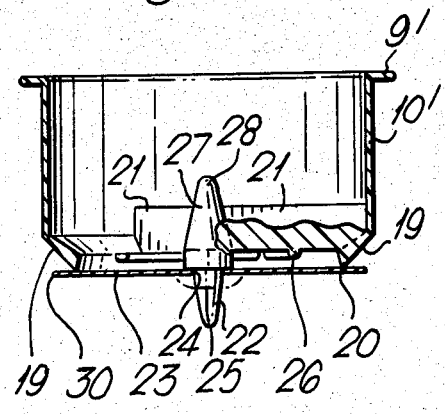
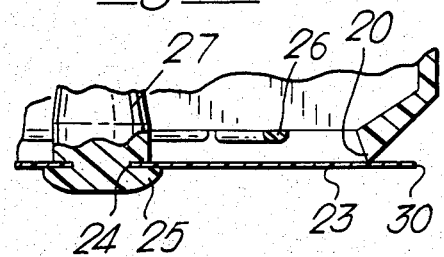
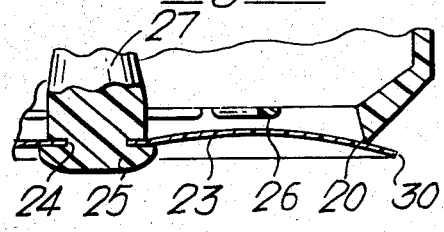
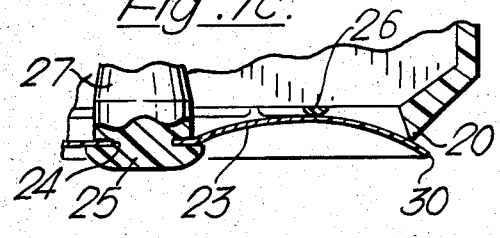

SPIROMETER ACCESSORY

This is a continuation of application Ser. No. 430,689 filed Sept. 30, 1982 and now abandoned; which in turn is a continuation of application Ser. No. 201,286 filed Oct. 27, 1980, now abandoned.

Spirometers by which the pattern of exhalation by a patient can be recorded are used as a diagnostic aid in clinical practice. It is usual, for hygenic reasons, to provide a spirometer with a disposable mouthpiece eg. of cardboard. This arrangement does not however eliminate the possibility of the patient inhaling, from the apparatus, air which is contaminated by matter from previous tests on other patients.

The present invention provides an inlet tube for a spirometer, said tube being fitted with a mouthpiece formed to engage the tube at the inlet end thereof, an apertured valve seating part carried by the mouthpiece and being formed to extend across the bore of the tube, a valve diaphragm formed of flexible material, said diaphragm being operable to obstruct a return flow of air blown through the mouthpiece and a radially extending part or parts for preventing reverse fitting of the mouthpiece to the tube.

The radially extending part may simply be a flange. In a more elaborate arrangement the flange has a sleeve part for engagement with the exterior of the tube, the flange extends inwardly from the sleeve part and the valve seating part is carried by the inner periphery of the flange.

In a preferred arrangement the seating part has an axially projecting circular rim for engagement with the peripheral region of the diaphragm. A major part of the force produced on the diaphragm by a (potential) reverse flow of air is carried by the rim to give an efficient sealing effect at low back-pressure with a diaphragm of economic construction.

Conveniently the seating part has a central mounting for mounting the diaphragm by its centre, said mounting being carried by spokes.

Best sealing results are obtained by mounting the diaphragm centrally at an axial position such that on its initial engagement with the circular rim produced by said return flow of air, said diaphragm is in a substantially un-distorted configuration. With a diaphragm of the most economic form ie. a planar form, this arrangement involves having the center of the diaphragm mounted in the plane of the rim.

Provision is required for maintaining an adequate sealing action for the increased back-pressures which develop after the initial sealing action and such relatively high back-pressures as may be produced by the patient sucking. For this purpose the seating part may be provided with an inner ring part mounted co-axially with the rim in an axially recessed position with the diaphragm deformable to engage the ring part after said initial engagement with the circular rim. With this arrangement, the efficient sealing action of the circular rim for low back-pressures is maintained. As the pressure increases, the diaphragm bulges. Such bulging action is limited by contact of the diaphragm with the inner ring. Such further bulging action between the periphery and the inner ring, and between the inner ring and the centre of the diaphragm, as may occur produces far less disturbance of the sealing action than does free bulging. By assisting the sealing action, the provision of the inner ring reduces the constructional requirements of the diaphragm and makes it possible to form the diaphragm from flexible resinous sheeting, eg. plasticised polyvinyl chloride sheeting. It is satisfactory to cut the diaphragm from resinous sheeting of the quality supplied in the form of rolls. In use the diaphragm is warmed by the patient's breath and when cut as aforesaid many forms of the sheeting tend to curl. For this reason the diaphragm is preferably oriented so that the potentially concave face of the sheeting is the face which engages the seating.

The inner ring, in promoting the sealing action of a diaphragm of low rigidity, also results in minimising the flow resistance of an exhalation into the spirometer. The inner ring itself can be discontinuous in form thus reducing its own flow resistance. By giving the spokes, aforesaid, a laminar configuration and orienting them with their edges facing the diaphragm, the flow resistance attributable to the spokes is reduced. Not only is the area of the spokes across the direction of flow minimised but the laminar form tends to reduce turbulence and the flow-resistance attributable thereto.

Having an even number of spokes is desirably avoided. It is found that with two or four spokes there is a tendency to induce a folding action on the diaphragm. An odd number, three spokes being the most convenient, gives best results.

The following description, in which reference is made to the accompanying drawings is given in order to illustrate the invention.

In the drawings:

FIG. 1 is a cross section showing the general arrangement of a first embodiment of the inlet tube in association with a spirometer, FIG. 2 is a cross section showing part of the embodiment 1 in further detail, FIG. 3 shows part of the embodiment in plane, FIG. 4 shows a second embodiment partly in elevation and partly in axial cross-section, FIG. 5 is an underneath plan of part of the embodiment of FIG. 4, FIG. 6 is a cross section taken along line VI—VI of FIG. 5, and FIG. 7A, B & C are diagrammatic cross-sections showing the diaphragm of the embodiment of FIGS. 4 to 6, its associated parts and its response to pressure FIG. 1 shows the known arrangement of a flexible tube 1 connected with a bellows-type spirometer shown diagrammatically at 2 and having a fitting 3 for receiving the end of a disposable cardboard tube 4.

In accordance with the invention, the tube 4 is fitted with a mouthpiece 5 (shown in further detail in FIGS. 2 and 3) having a valve diaphragm 6 on the spirometer-side of a seating 7. Seating 7 is mounted in a recessed position within a sleeve part 8 which slides over the exterior of tube 4. Sleeve part 8 terminates in a radially inwardly projecting flange 9 the inner periphery of which carries an inner sleeve part 10 which engages the interior of tube 4 and carries seating 7. The sleeve parts 8 and 10, the flange 9 and seating 7 are formed in a single piece from aluminium or a thermoplastic resin.

On the spirometer side, seating part 7 has a projecting circular rim 11 for engagement with the periphery of diaphragm 6. A central hole 12 serves for mounting the diaphragm by a rivet (13 in FIG. 1). Apertures 14 in seating 7 admit air to flex the diaphragm 6 away from seating 7 when the patient exhales for a test. Return flow from tube 1 is prevented by sealing contact of diaphragm 6 with rim 11. Parts 15 of the seating 7 prevent major distortion of the diaphragm.

Mouthpiece 7, like the tube 5, is an expendable accessory. Its design is comfortable for the patient (edges 16 and 17 are rounded), and flange 9 (and in the case shown, also sleeve 8) prevents reverse fitting to tube 4.

The embodiment of FIGS. 4 to 7C has a simple flange $9^1$ for engagement with the end of cylindrical cardboard tube 4 (internal diameter 28 mm) when the inner sleeve part $10^1$ is fully inserted. Flange $9^1$ projects radially outwardly beyond tube 4 as shown in FIG. 4. End 18 of tube 4 has a firm mating fit within the fitting 3 shown in FIG. 1 and reverse-fitting is prevented by projection $9^1$.

The inner end of sleeve part $10^1$, ie. that end which fits within tube 4, is formed with a convergent portion 19 which terminates in a circular rim 20 projecting in the axial directions of sleeve part $10^1$ and tube 4. Internally, the inner end of the sleeve part has three radial spokes 21 of laminar cross-section which locate a central mounting 22 for a circular diaphragm 23 cut from plasticised polyvinylchloride sheeting—of thickness 0.25 mm. As shown in FIG. 6 the mounting is generally tapered to receive a circular hole 24 punched through the centre of the diaphragm. The diaphragm is retained by subsequent forming the mounting to a mushroom shape 25 as shown in FIGS. 7A, 7B and 7C and also, in broken lines, in FIG. 6.

Spokes 21 have their major and minor dimensions of cross-sections oriented in the axial direction (FIG. 6) and the circumferential direction (FIG. 5) respectively. In this way their flow resistance is minimised and they also act to smoothout turbulence.

On their edges facing the diaphragm, the spokes carry a concentric ring 26.

Inner sleeve part $10^1$ with its flange $9^1$ its rim 20, the spokes 21, ring 26, mounting 22 for the diaphragm and a central boss 27 are formed as an integral injection moulding of a thermoplastic resin, eg. polystyrene, polyethylene, polypropylene or polyvinyl chloride. Part 28 (FIG. 6) which is of conical form as far as the diaphragm mounting 22 serves as the resin entry from the moulding tool. The flow of resin to form the sleeve part $10^1$ and parts $9^1$, 19, 21 and 26 is from resin entry part 28 via spokes 21. Having the spokes in the laminar form described instead of merely with a lesser dimension in the axial direction of the sleeve part which is sufficient to support the boss 27 provides an adequate flow of resin in the moulding operation besides smoothing turbulence and giving a low resistance to the exhalation of the patient. This applies even though only three spokes are provided for the reason aforesaid. Ring 26 is an incomplete ring with gaps 29 (FIG. 5). These gaps which do not interfere in any significant way with the action required of the ring, are found to lead to reliable formation of the ring in the moulding operation.

The exhalation flow of a patient through tube 4 into a spirometer, flexes the diaphragm away from rim 20 giving a negligible flow resistance.

When the pressure on the spirometer side of the diaphragm is greater than or equal to that within the sleeve part $10^1$, the peripheral region of the diaphragm engages the rim 20. The force on the diaphragm is opposed by reaction with rim 20 and central mounting 22. Rim 20 has a radius of curvature of only 0.2 mm and provides a substantially gas-tight seal (FIG. 7A). Further increase of the pressure causes the diaphragm to bulge, FIG. 7B, with the force still opposed as before. The flexibility of the diaphragm is such that the bulging as the pressure increases substantially would drag the peripheral region clear of rim 20. Before this can happen, the bulging diaphragm engages ring 21. Subsequent bulging is then over two separate concentric parts of the diaphragm as shown in exaggerated form in FIG. 7C causing subsequent radial contraction to be at a reduced rate so that the edge 30 of the diaphragm remains outwardly of the rim 20.

Having the rim 20 formed on convergent portion 19 of sleeve $10^1$ enables the diaphragm to have an adequate diameter without contacting the interior of tube 4.

FIGS. 7A, B & C have an enlarged scale in the direction of flow for clarity of illustration.

It will be understood that the specific constructions described herein are given by way of examples only and that once the principles have been understood various modifications may be made by those skilled in the art without departing from the scope of the invention claimed.

I claim:

1. An inlet for use with a spirometer responsive to the exhalation flow of breath gases from a patient, said inlet comprising an inlet tube having an inlet end for the entry of said exhalation flow and an outlet end for connection to the spirometer; a mouthpiece having a first and second end and an internal bore, said mouthpiece being in engagement at its first end with said inlet end of said inlet tube as an exhalation flow inlet thereto; an apertured valve seating member carried by said mouthpiece and being formed to extend across said bore; a valve diaphragm formed of thin flexible material, said diaphragm having a peripheral region, a central region and an intermediate region between said peripheral region and said central region; said valve seating member having an axially projecting outer rim and a diaphragm mounting means positioned within said outer rim, said diaphragm mounting means having a central mount and at least three radially extending spokes connected between said central mount and said sidewall for retaining said diaphragm by said central region thereof in an axial position such that said diaphragm flexes toward the outlet end of said inlet tube and said diaphragm lies in a first plane with said peripheral region of said diaphragm in sealing engagement with said outer rim; said spokes having cross-sections that provide laminar flow therearound in a direction from said first end to said second end of said mouthpiece to minimize flow resistance therethrough; said diaphragm mounting means further including inner members extending laterally from each of said spokes, said spokes and said inner members being axially displaced from said first plane in a direction toward the first end of said mouthpiece such that said inner members lie in a second plane parallel to and axially displaced from said first plane whereby, under zero flow conditions, said diaphragm lies in said first plane and engages only said outer rim and, under reverse flow conditions, said diaphragm distorts and engages said inner members at said intermediate region thereof thereby preventing disengagement of said diaphragm from sealing engagement with said outer rim.

2. An inlet according to claim 1 wherein the first end of said mouthpiece is slideably fitted into said inlet tube at said inlet end and includes at its second end a radially extending element for preventing the fitting of said second end of said mouthpiece into a spirometer.

3. An inlet according to claim 2 wherein said radially extending element is a flange.

4. An inlet according to claim 1 wherein said apertured valve seating member has an inner ring part mounted coaxially with said outer rim in an axially recessed position, and said diaphragm is deformable to engage said inner ring.

5. An inlet according to claim 4 in which the inner ring part is discontinuous.

6. An inlet according to claim 1 in which said diaphragm is formed from flexible resinous sheet material.

7. An inlet according to claim 6 in which the resinous sheet material is of a kind which curves on heating to a configuration having a concave face and a convex face and the diaphragm is oriented so that the potentially concave face of the sheeting is the face which engages the seating.

8. An inlet according to claim 1 in which the said diaphragm is formed from flexible plasticized polyvinyl chloride sheeting.

* * * * *